US005895654A

United States Patent [19]
Hartford et al.

[11] Patent Number: 5,895,654
[45] Date of Patent: Apr. 20, 1999

[54] STREPTOCOCCUS EQUI VACCINE

[75] Inventors: Orla Mary Hartford, Duleek; Timothy James Foster, Dublin, both of Ireland; Antonius Arnoldus Christiaan Jacobs, Kessel, Netherlands

[73] Assignee: Provost Fellows & Scholars of the College of the Univ. of the Holy Undivided Trinity of Queen Elisabeth, Dublin, Ireland

[21] Appl. No.: 08/789,727

[22] Filed: Jan. 27, 1997

[30] Foreign Application Priority Data

Jan. 25, 1996 [EP] European Pat. Off. ............. 96200171

[51] Int. Cl.⁶ .................................................. A61K 39/085
[52] U.S. Cl. ........................................................ 424/237.1
[58] Field of Search ........................... 424/184.1, 237.1; 435/172.1, 253.4, 885

[56] References Cited

U.S. PATENT DOCUMENTS

| | | |
|---|---|---|
| 4,110,433 | 8/1978 | Purdy . |
| 4,582,798 | 4/1986 | Brown et al. . |
| 4,788,059 | 11/1988 | Usdin . |
| 5,183,659 | 2/1993 | Timoney . |
| 5,294,441 | 3/1994 | Curtiss . |
| 5,389,368 | 2/1995 | Curtiss . |
| 5,468,485 | 11/1995 | Curtiss . |
| 5,612,042 | 3/1997 | Jacobs . |
| 5,672,345 | 9/1997 | Curtiss . |
| 5,674,499 | 10/1997 | Willemse et al. . |

FOREIGN PATENT DOCUMENTS

Wo 87/00436  1/1987  WIPO .

OTHER PUBLICATIONS

Bernadette, et al. J. General Microbiol 137:2125–2133, 1991.
Timoney et al. In: Recent Advances in Streptococci & Streptococcal Diseases. Eds. Kimumetal pp. 294–295, 1985.
Chanter et al, Vet Microbiology 43:209–218, 1995.
Curtiss et al. Res. Microbial 141:797–805, 1990.

*Primary Examiner*—Nita Minnifield
*Attorney, Agent, or Firm*—Mary E. Gormley

[57] ABSTRACT

The present invention relates to a live attenuated strain of the bacterium *Streptococcus equi*, a pathogen causing strangles in horses. The invention also relates to a vaccine against strangles, methods for the preparation of such a vaccine and to the use of the strain for the preparation of such a vaccine.

11 Claims, No Drawings

STREPTOCOCCUS EQUI VACCINE

The present invention is concerned with a new strain of *Streptococcus equi*, and a vaccine comprising this strain.

*Streptococcus equi* has been known for a long time to be the cause of an acute disease of the upper respiratory tract in horses (Sweeney et al., *Compendium Equine* 9: 689–693 (1987)). This highly contagious disease is characterised by fever, mucopurulent nasal discharge, lymphadenopathy and subsequent abscessation of the lymph nodes of the head and the neck (Sweeney et al., *Compendium Equine* 9: 845–851 (1987)). The swelling of the lymph nodes is often so severe that the airways become obstructed. This phenomenon explains the common name of the disease; strangles. The disease is only fatal in a minority of the cases, as described by Sigmund (Sigmund, O. H. and Fraser, C. M. eds.: *The Merck Veterinary Manual*, 5th Ed. Merck and Company Inc., Rahway, N.J.: 313–315 (1979)).

Contrary to this, morbidity is generally high, and can be as high as 100% in susceptible populations.

Vaccines against the disease have also been known for a long time (Bazely, P. L.; *Austr. Vet. J.* 16: 243 (1940)) and (Bazely, P. L.; Austr. Vet. J. 18: 141–155 (1942).

Until now, only two kinds of vaccines are available: a) vaccines based on classical bacterins and b) sub-unit vaccines based on the M-protein, an immunogenic protein.

Both kinds of vaccine have their own severe drawbacks. Bacterins are notorious for their adverse reactions and are known to provide relatively little protection (Subcommittee on the Efficacy of Strangles Bacterin, Report, American Association of Equine Practitioners). M-protein has been considered a weak antigen, only providing a satisfactory immune response after multiple injections. (Shrivastava, S. K. and Barnum, D. A.; *Can. J. Comp. Med.* 49: 351–356 (1985)) (Woolcock, J. B.: *Austr. Vet. J.* 51: 554–559 (1975)).

In addition, the duration of immunity obtained by these vaccines is relatively short; further booster vaccinations should be given at least once a year (Sweeney et al., *Compendium Equine* 9: 845–851 (1987)).

Classical vaccines based on bacterins or subunits are e.g. available trough Forth Dodge Laboratories and Coopers Animal Health. Furthermore, the Mobay Company owns e.g. U.S. Pat. No. 4,944,942 disclosing a bacterin.

When horses are naturally infected by a live virulent *Streptococcus equi* field strain, they develop a long-lasting immunity. This is the case even when the infection passes without clinical signs (Woolcock, J. B.: *Austr. Vet. J.* 51: 554–559 (1975)). This means that in principle, vaccination with a live attenuated strain would be highly advantageous over vaccination with the currently used inactivated or sub-unit-vaccines.

In spite of this fact, however, there is currently no live attenuated vaccine commercially available.

Only one patent (EP 0.230.456) is known, in which a vaccine based on a specific live attenuated *Streptococcus equi* strain is claimed. No commercial vaccines based on this patent have been put on the market yet, although the patented strain exists for 10 years now.

The vaccine of patent EP 0.230.456, although better than the existing bacterin and sub-unit vaccines, has several drawbacks:

a) the attenuated character is based on chemically induced, non-defined mutations in the genome of the vaccine strain. These mutations are almost certainly point-mutations, due to the used mutagens: nitrosoguanidine. Point-mutations are prone to back-mutation and thus to reversion to virulence. An attenuated strain in which attenuation is caused by a well-defined irreversible deletion of substantial size, and thus not capable of reverting to virulence would therefore be highly preferred.

b) the vaccine is based on a non-encapsulated strain: screening was done for non-encapsulated colonies. Their loss of virulence is the basis for the vaccine. As a consequence, a vaccine based thereon would thus not protect against one apparent virulence factor i.e. the capsule.

A live vaccine still comprising the capsule, and thus providing a more complete protection, would therefore be preferred.

c) the vaccine is not fully safe in foals. Since however foals are the most susceptible to the disease, they should be vaccinated at a very young age. Therefore a vaccine that is completely safe in foals should be highly advantageous.

Surprisingly it was found that a new strain, derived from a wild type field isolate possesses the above mentioned advantageous characteristics.

This new strain was derived from a virulent field strain, strain TW, that was isolated from a clinically ill horse.

The new strain was selected based on the fact that it comprises a large deletion in its genome, causing its attenuated character in comparison with the parent TW strain. Since the deletion is about 1 kb, the chances that reversion to virulence occurs are negligible. The strain still retains its capsule. Also, it is safe for foals, as is shown in the Examples.

The invention provides *Streptococcus equi* strain TW 928, as deposited on Dec. 12, 1995, under number CBS 813.95 with the Centraalbureau voor Schimmelcultures, P.O. box 273, 3740 AG Baam, The Netherlands.

The invention further relates to a microbiological pure culture comprising bacteria according to the deposited strain. It goes without saying that next generations of bacteria from the deposited strain are also included.

The culture can e.g. be obtained by growing said bacteria at a temperature between 30 and 41° C. Bacteria can be grown e.g. in M17 medium (1 L contains 5 g Tryptose, 5 g neutralized soy peptone, 2.5 g yeast extract, 5 g beef extract, 10 g glucose, 0.5 g ascorbinic acid, 19 g Na2(B-)glycerophosphate, 0.25 g MgSO4(7H2O), pH 7.0–7.2).

The invention further provides a live vaccine for combating Streptococcus infection in horses. Such a vaccine comprises attenuated live bacteria of the *Streptococcus equi* strain TW 928, deposited under number CBS 813.95 with the Centraalbureau voor Schimmelcultures at Baam, The Netherlands and a pharmaceutically acceptable carrier. Such a carrier may be as simple as water, but it may e.g. also comprise culture fluid in which the bacteria were cultured. Another suitable carrier is e.g. a solution of physiological salt concentration.

The vaccine according to the present invention can be administered in various forms. It can e.g. be administered parenterally, e.g. intramuscularly, subcutaneously or intradermally, it can also be given orally or it can be given intranasally. The nasal mucosa is the most common porte d'entree for *Streptococcus equi* infections. Therefore, the nose is the most natural place for the application of the live attenuated vaccine according to the invention. In addition, this application site has the advantage that it is easily reached, and that the vaccine can e.g. be administered by spraying. Thus, in a preferred form, the vaccine of the present invention is suitable for intranasal application.

The vaccine may comprise any dose of bacteria, sufficient to evoke an immune response. Doses ranging between $10^3$ and $10^9$ bacteria are e.g. very suitable doses.

Due to its attenuated characteristics, the vaccine can be used to protect horses at any age, including new-born horses. For practical reasons, the vaccine will usually be given at young age, e.g. between 1 and 12 month of age.

There are several ways to store live organisms. Storage in a refrigerator is e.g. a well-known method. Also often used is storage at –70° C. in a buffer containing glycerol. Bacteria can also be kept in liquid nitrogen. Freeze-drying is another way of conservation. Freeze-dried bacteria can be stored and kept viable for many years. Storage temperatures for freeze-dried bacteria may well be above zero degrees, without being detrimental to the viability.

Freeze-drying can be done according to all well-known standard freeze-drying procedures. Optional beneficial additives, such as e.g. skimmed milk, trehalose, gelatin or bovine serum albumin can be added in the freeze-drying process. Therefore, in a more preferred form, the vaccine is in a freeze-dried form.

In another embodiment, the vaccine of the present invention additionally comprises another attenuated pathogen or antigenic material from another pathogen. Such a pathogen may e.g. be another bacterium or a parasite. Also it can be of viral origin. Usually, the other pathogen or antigenic material thereof will be a horse pathogen. A vaccine according to the invention that also comprises such an additional attenuated pathogen or antigenic material from another pathogen has the advantage that it induces protection against several infections at the same time. Horse pathogens or antigenic material thereof that can advantageously be added are e.g. Potomac fever agent, *Rhodococcus equi*, *Clostridium tetanii*, *Mycobacterium pseudomallei*, Vesicular Stomatitis Virus Borna disease virus, Equine influenza virus, African horse sickness virus, Equine arteritis virus, Equine herpesvirus 1-4, Infectious anemia virus, Equine encephalomyelitis virus and Japanese B encephalomyelitis virus.

The vaccine may also comprise an adjuvans. Adjuvantia are non-specific stimulators of the immune system. They enhance the immune response of the host to the invading pathogen. Examples of adjuvantia known in the art are Freunds Complete and Incomplete adjuvans, vitamin E, non-ionic block polymers, muramyldipeptides, ISCOMs (immune stimulating complexes, cf. for instance EP 109942), Quill A, mineral oil, vegetable oil, and Carbopol (a homopolymer).

Adjuvantia, specially suitable for mucosal application are e.g. the *E. coli* heat-labile toxin (LT) or Cholera toxin (CT).

In addition, the vaccine may comprise one or more stabilisers. Also, the vaccine may comprise one or more suitable emulsifiers, e.g. Span or Tween.

Also the invention provides methods for the preparation of a vaccine. These methods e.g. comprise admixing bacteria of *Streptococcus equi* strain TW 928 and a pharmaceutically acceptable carrier.

Further the present invention relates to the use of the *Streptococcus equi* strain TW 928, deposited under number CBS 813.95 with the Centraalbureau voor Schimmelcultures at Baarn, The Netherlands for the preparation of a vaccine for combating Streptococcus infection in horses.

EXAMPLES

Example 1:

Selection of a mutant strain.

A field strain of *Streptococcus equi* was isolated from a horse with clinical signs of strangles.

This strain was grown overnight, aerobically at 37° C., on blood agar and then inoculated in M17 medium (1 L contains 5 g Tryptose, 5 g neutralised soy peptone, 2.5 g yeast extract, 5 g beef extract, 10 g glucose, 0.5 g ascorbinic acid, 19 g Na2(B-)glycerophosphate, 0.25 g MgSO4 (7H2O), pH 7.0–7.2), and subjected to various DNA mutation techniques. Classical mutation techniques have e.g. been described by Carlton, B. C. and Brown, B. J. in Manual of Methods for General Bacteriology (Eds. Gerhardt et al) American Society for Microbiology, Washington D.C., p. 226 (1981). Mutation techniques based on recombinant DNA technology are described in Maniatis (Maniatis, Molecular Cloning, Cold Spring Harbour Laboratory Press, ISBN 0-87969-309-6 (1989)).

Mutant strains having deletions detectable in standard restriction fragment polyacrylamide gel electrophoresis (well-known in the art, e.g. Maniatis) as compared to the parent TW strain were selected.

A strain with a 1 kb deletion was selected, designated TW 928 and tested for its attenuated character as described in the Examples below.

Example II:

Preparation of vaccine

*Streptococcus equi* strain TW 928 and the wild type parent TW strain were grown overnight, aerobically at 37° C., on blood agar and then inoculated in M17 medium. For the vaccination/challenge studies, the strains were cultured for 6 hours at 37° C. and pH 7.4 in 100 ml of M17 medium, centrifuged and resuspended in PBS. Total count was determined in a counting chamber and viable count was detected by plate counting. Cultures used for vaccination/challenge contained about $10^9$ bacteria/ml or ten-fold dilutions thereof.

Example III:

Safety test of the vaccine strain TW 928 in mice

In this example, the rate of attenuation of a *S. equi* mutant TW 928 as compared to the wild-type strain TW has been tested in mice. Different concentrations of CFU of the mutant strain as well as the parent TW wild-type strain were applied intranasally or intraperitoneally to mice and mortality was recorded.

Animals

BALB/c mice, 8 weeks of age, obtained from IFFA-Credo, were used for the experiment.

Treatment

At 8 weeks of age, 1 group of 19 mice was challenged intranasally (50 µl) with *S. equi* strain TW and 1 group of 20 mice was treated intranasally with *S. equi* strain TW 928 (see Table 1).

At 8 weeks of age, 6 groups of 10 mice each were challenged intraperitoneally with 250 µl of 10-fold dilutions of a *S. equi* strain TW culture and 6 groups of 10 mice each were challenged intraperitoneally with 250 µl of 10-fold dilutions of a *S. equi* strain TW 928 culture (see Table 1). After the treatments, mortality was recorded during 35 days.

Vaccination/challenge cultures

Both *S. equi* strain TW and TW 928 were grown overnight, aerobically at 37° C., on blood agar and then inoculated in M17 medium. For the vaccination/challenge, fresh cultures (5–6 hours old) containing about $10^9$ bacteria/ml or 10-fold dilutions thereof were used. Total count was determined in a counting chamber and viable count was determined by plate counting. For actual vaccination/challenge dose see Table 1.

Results:

The results after intraperitoneal and intranasal challenge of 8 weeks old mice with strain TW or strain TW 928 are shown in Table 2. The $LD_{50}$ of the mutant strain after intraperitoneal challenge, appeared about $10^4$ times higher as compared to the wild-type strain. Likewise, after intranasal application, the mutant strain appeared significantly attenuated as compared to the wild-type. At high doses of both strains, mice died within 24 hours, possibly due to an overdose of toxic substances. At lower doses of the wild-type strain most mice died at 5 to 9 days after challenge, presumably due to infection (Table 2). In contrast, at lower doses of the mutant strain almost no mice died later then 2 days post challenge (except for 3 out of 60 mice), indicating that the mutant strain in most cases does not cause a fatal infection (and is less infectious compared to the wild-type).

After intranasal challenge with the wild-type, most mice died between 5 and 8 days after treatment due to infection since all these mice had shown severe neurological signs. In contrast, after intranasal challenge with the mutant strain, only 3 of 20 mice died within 24 hours, possibly due to an overdose of toxic substances rather than infection (table 2).

Example IV:

Protection test of the vaccine strain TW 928 in mice

In this example, the potential immunogenicity of a S. equi mutant has been tested in mice. Immunity induced by the mutant strain after intranasal vaccination was challenged with a lethal intranasal dose of the parent TW wild-type strain.

Different concentrations of CFU of the mutant strain as well as the parent TW wild-type strain were applied intranasally to mice and mortality was recorded.

Immunity induced by two intranasal vaccinations with strain TW 928 was challenged with the wild-type strain TW. (1 week after booster vaccination).

Animals

BALB/c mice, 6 weeks of age, obtained from IFFA-Credo, were used for the experiment.

Housing

One week before the start of the experiment the mice were housed in cages (10 mice/age) in negative pressure isolators for acclimatisation. One group of 21 mice was housed in a clean room until 9 weeks of age (day of challenge)= unvaccinated control group.

Treatment

At 6 weeks of age, 4 groups of 10 mice were treated intranasally with 50 µl of different *S. equi* strain TW preparations: 1) whole culture, 2) whole culture 10× diluted in culture medium, 3) cells (culture strength) suspended in PBS or 4) cells in PBS 10× diluted relative to culture strength (see Table 3). The same procedure was done for *S. equi* strain TW 928, except that for the cells in PBS at culture strength, 30 mice were used (see Table 3). A group of 21 mice (housed separately in a clean room) was left untreated. After treatment, mortality was recorded during 14 days. At 8 weeks of age, the survivors of the strain TW 928 treated groups were again treated (boosted) intranasally with the mutant strain as described for the priming with freshly prepared preparations. After the booster, mortality was recorded for 7 days. At 9 weeks of age (one week after the booster), survivors were challenged intranasally with *S. equi* strain TW together with the untreated control group and mortality was recorded during 14 days (see Table 3).

Vaccination/challenge cultures

Both *S. equi* strains were grown overnight, aerobically at 37° C., on blood agar and then inoculated in M17 medium. For the vaccination/challenge, fresh cultures (5–6 hours old) or (freshly centrifuged) cells suspended in PBS at culture strength containing about $10^9$ bacteria/ml or 10-fold dilutions thereof were used. Total count was determined in a counting chamber and viable count was determined by plate counting. For actual vaccination/challenge dose see Table 3.

Results:

The results after intranasal treatment with the wild-type or mutant strain are shown in Table 4. Practically all mice challenged with the different wild-type TW preparations died whereas only 7 out of 60 (all except one within 24 hours) mice died after intranasal treatment with the mutant strain TW 928 (Table 4). Two weeks after priming the survivors of the mutant treated groups were boosted. All boosted mice survived until challenge, except for 3 mice of the TW928-in-PBS group. One week after booster vaccination, the survivors as well as 21 age and source matched control mice were challenged intranasally with the wild-type strain. After challenge all control mice died whereas the different vaccinated groups showed different degrees of protection, up to 91% (Table 5). The protection seems dose dependent since the mice vaccinated with the 10× diluted preparations showed less protection. Two weeks after challenge more than half of the vaccinated survivors had cleared the challenge strain from the throat and in most cases the brains appeared sterile (Table 6).

CONCLUSION

From the results of Examples III and IV it can be concluded that *S. equi* strain TW 928 is significantly attenuated as compared to the parent wild-type strain TW, when tested in mice (intranasal route as well as intraperitoneal route). Furthermore, twice intranasal vaccination with the mutant strain induces protection against a lethal intranasal challenge with the wild-type strain.

TABLE 1

| Experimental design Example III | | | |
|---|---|---|---|
| | Treatment at 8 weeks of age | | |
| No. of mice | Challenge route | Strain[a] | CFU/dose |
| 19 | IN[b] | TW | $3.1 \times 10^7$ |
| 20 | IN | TW 928 | $3.4 \times 10^7$ |
| 10 | IP[c] | TW | $7.7 \times 10^6$ |
| 10 | IP | TW | $7.7 \times 10^5$ |
| 10 | IP | TW | $7.7 \times 10^4$ |
| 10 | IP | TW | $7.7 \times 10^3$ |
| 10 | IP | TW | $7.7 \times 10^2$ |
| 10 | IP | TW | $7.7 \times 10^1$ |
| 10 | IP | TW 928 | $4.3 \times 10^7$ |
| 10 | IP | TW 928 | $4.3 \times 10^6$ |
| 10 | IP | TW 928 | $4.3 \times 10^5$ |
| 10 | IP | TW 928 | $4.3 \times 10^4$ |
| 10 | IP | TW 928 | $4.3 \times 10^3$ |
| 10 | IP | TW 928 | $4.3 \times 10^2$ |
| 15 | untreated controls | | |

[a]ND = intranasal (50 µl)
[b]IP = intraperitoneal (250 µl)

TABLE 2

| Mortality after challenge/vaccination with *S. equi* strain TW 928 | | | | |
|---|---|---|---|---|
| No. of mice | Challenge route | Strain | CFU/dose | Total mortality |
| 19 | IN | TW | $3.1 \times 10^7$ | 19 |
| 20 | IN | TW 928 | $3.4 \times 10^7$ | 3 |
| 10 | IP | TW | $7.7 \times 10^6$ | 10 |
| 10 | IP | TW | $7.7 \times 10^5$ | 10 |
| 10 | IP | TW | $7.7 \times 10^4$ | 10 |
| 10 | IP | TW | $7.7 \times 10^3$ | 10 |
| 10 | IP | TW | $7.7 \times 10^2$ | 8 |
| 10 | IP | TW | $7.7 \times 10^1$ | 6 |
| 10 | IP | TW 928 | $4.3 \times 10^6$ | 10 |
| 10 | IP | TW 928 | $4.3 \times 10^5$ | 3 |
| 10 | IP | TW 928 | $4.3 \times 10^4$ | 1 |
| 10 | IP | TW 928 | $4.3 \times 10^3$ | 0 |
| 10 | IP | TW 928 | $4.3 \times 10^2$ | 0 |

LD50 IP challenge strain TW $7.7 \times 10^1$ CFU (Reed & Munch) $5.3 \times 10^1$ CFU (Probit analysis, Finney)
LD50 IP challenge strain TW 928 $7.0 \times 10^5$ CFU (Reed & Munch) $4.9 \times 10^5$ CFU (Probit analysis, Finney)

TABLE 3

Experimental design Example IV

| No. of | Intranasal treatment (50 μl) at 6 weeks of age | | Intranasal treatment (50 μl) at 8 weeks of age | | Intranasal treatment (50 μl) at 9 weeks of age | |
|---|---|---|---|---|---|---|
| mice | Strain | CFU/dose | Strain | CFU/dose | Strain | CFU/dose |
| 10 | TW whole culture | $2.3 \times 10^8$ | | | | |
| 10 | TW whole culture 10x[a] | $2.3 \times 10^7$ | | | | |
| 10 | TW in PBS | $2.1 \times 10^8$ | | | | |
| 10 | TW in PBS 10x[b] | $2.1 \times 10^7$ | | | | |
| 10 | TW 928 whole culture | $2.5 \times 10^8$ | TW 928 whole culture | $2.3 \times 10^8$ | TW whole culture | $3.7 \times 10^8$ |
| 10 | TW 928 whole culture 10x[a] | $2.5 \times 10^7$ | TW 928 whole culture 10x[a] | $2.3 \times 10^7$ | TW whole culture | $3.7 \times 10^8$ |
| 30 | TW 928 in PBS | $0.9 \times 10^8$ | TW 928 in PBS | $2.8 \times 10^8$ | TW whole culture | $3.7 \times 10^8$ |
| 10 | TW 928 in PBX 10x[b] | $0.9 \times 10^7$ | TW 928 in PBX 10x[b] | $2.8 \times 10^7$ | TW whole culture | $3.7 \times 10^8$ |
| 21 | untreated controls | — | untreated controls | — | TW whole culture | $3.7 \times 10^8$ |

[a]10x diluted in culture medium
[b]10x diluted in PBS

TABLE 4

Mortality after challenge/vaccination with *S. equi* strain TW or TW 928.

| Intanasal treatment (50 μl) at 6 weeks of age | CFU/dose | No. of mice | Total mortality | % mortality |
|---|---|---|---|---|
| TW whole culture | $2.3 \times 10^8$ | 10 | 10 | 100 |
| TW whole culture 10× | $2.3 \times 10^7$ | 10 | 10 | 100 |
| TW in PBS | $2.1 \times 10^8$ | 10 | 10 | 100 |
| TW in PBS 10× | $2.1 \times 10^7$ | 10 | 6 | 60 |
| TW 928 whole culture | $2.5 \times 10^8$ | 10 | 2 | 20 |
| TW 928 whole culture 10× | $2.5 \times 10^7$ | 10 | 0 | 0 |
| TW 928 in PBS | $0.9 \times 10^8$ | 30 | 5 | 17 |
| TW 928 in PBS 10× | $0.9 \times 10^7$ | 10 | 0 | 0 |

TABLE 5

Mortality of mice after vaccination with *S. equi* strain TW 928 and challenge with strain TW

| Intranasal treatment with S. equi TW 928 at T = 0 and T = 2 weeks | No. of mice at T = 3 w[a] | Total mortality | % protection |
|---|---|---|---|
| whole culture | 8 | 1/8 | 87.5 |
| whole culture 10× | 10 | 3/10 | 70 |
| in PBS | 22 | 2/22 | 91 |
| in PBS 10× | 10 | 6/10 | 40 |
| unvaccinated controls | 21 | 21/21 | 0 |

[a]day of challenge with strain TW, mice 9 weeks old

TABLE 6

Bacterial re-isolation results of survivors 14 days after challenge (see Table 5).

| Intranasal treatment with *S. equi* 928 at | No. of | Re-isolation of *S. equi* from | | Total |
|---|---|---|---|---|
| T = 0 and T = 2 weeks | mice | throat | brains | positive |
| whole culture | 7 | 3 | 1 | 3/7 |
| whole culture 10× | 7 | 2 | 1 | 3/7 |
| in PBS | 20 | 7 | 3 | 9/20 |
| in PBX 10× | 4 | 1 | 1 | 2/4 |
| unvaccinated controls | 0 | — | — | — |

Example V:

Safety test of the vaccine strain TW 928 in horses

*Streptococcus equi* strain TW 928 was tested in six serologically negative horses for safety.

Animals

Six horses, 7–8 month of age, with no history of strangles were used.

Vaccination/challenge

At T=0 all six horses were exposed to a continuous aerosol of strain TW 928 using a Devilbiss nebulizer (operating at maximal setting) equipped with a mouth adapter. Each horse was exposed to the aerosol during 10 minutes (about 20 ml of a diluted 6 hours culture containing about $10^9$ CFU/ml was used for each horse). Thereafter, the culture was applied intranasally (5 ml/nostril) using a silicon tubing (about 25 cm) and a 10 ml syringe. The culture consisted of a six hours culture in M17 medium containing $2.3\times10^9$ CFU/ml which was 3× diluted with sterile NaCl just before use. This dilution was necessary to obtain a good aerosol. During 10 min. about 23 ml of this culture was aerosolised.

Clinical examination

Before vaccination and twice weekly after vaccination, the horses were clinically examined.

Post mortem examination

At T=4 w after vaccination, all horses were killed and subjected to post mortem examination. From each horse swabs for bacteriological examination were taken from guttural pouch, larynx, trachea, submandibular lymph nodes, retropharyngeal lymph nodes, parotic lymph nodes and tracheo-bronchial lymph nodes and further from all abnormalities (lesions) whether or not typical for strangles. Guttural pouch, larynx and trachea were swabbed directly and streaked onto blood agar. Tissue samples (i.e. lymph nodes) were cauterised, an incision was made using sterile scalpels, a swab was inserted and the material was streaked onto blood agar. The blood agar plates were incubated aerobically at 37° C. for 18–24 hours. Several haemolytic colonies (of different morphological types, if present) were cloned and tested in an API-strep and in 4 sugar tubes: sorbitol, ribose, lactose and trehalose.

Tissue samples for histological examination were taken from guttural pouch, submandibular lymph nodes, retropharyngeal lymph nodes, parotic lymph nodes and tracheobronchial lymph nodes and further from trachea or lung tissue in case of abnormalities.

RESULTS

Clinical signs

In the aerosol safety test model, using the parent TW wild-type strain, susceptible horses develop typical signs of strangles within 5-7 days, characterised by sudden high temperatures (>40° C.) and abscess formation of the mandibular and pharyngeal lymph nodes. No such signs were observed in the horses of the present experiment after vaccination. Temperatures did not exceed 39.5° C. except for horse 97 which had 39.7° C. at 18 days after vaccination. The submandibular lymph nodes of all horses appeared normal during the experiment except for horse 101 from which the left submandibular lymph node appeared slightly enlarged 2 days and 16 days after vaccination and from which the right submandibular lymph node appeared slightly enlarged at 11 days after vaccination. In contrast to the submandibular lymph nodes, the retropharyngeal lymph nodes can only be palpated indirectly. Except for horse no. 98 the retropharyngeal region of all horses appeared slightly to moderately enlarged during a few days.

Bacterial isolation from nasal washes

After vaccination S. equi was hardly isolated from the horses. Only from horse 100 and 101 the bacterium was re-isolated from nasal washes during the experiment and from horse 96 only at one occasion (See table 7).

Post-mortem examination and bacteriology

Four weeks after vaccination, all six horses were killed and subject to post-mortem examination and bacteriology. None of the horses showed any signs of strangles i.e. all lymph nodes appeared normal and from none of the horses (except for nasal washings at day of necropsy in two horses) Streptococcus equi was re-isolated.

TABLE 7

Re-isolation of S. equi from nasal washes,

| Horse No. | Re-isolation of S. equi (CFU/ml) at | | | | |
|---|---|---|---|---|---|
|  | T = 0 | T = 1W | T = 2W | T = 3W | T = 4W |
| 96 | — | — | $1 \times 10^3$ | — | — |
| 97 | — | — | — | — | — |
| 98 | — | — | — | — | — |
| 99 | — | — | — | — | — |
| 100 | — | $2 \times 10^5$ | $<10^2$ | $1 \times 10^4$ | $4 \times 10^4$ |
| 101 | — | $2 \times 10^4$ | $8 \times 10^6$ | — | $2 \times 10^6$ |

Histological examination

Histological examination of the mandibular, pharyngeal, parotic and tracheobronchial lymph nodes confirmed the macroscopic findings: no signs of strangles, i.e. no abscess formation. Nearly all lymph nodes that were examined were described as reactive lymphoid tissue with mild to moderate follicular (germinal centres) hyperplasia indicative for antigenic stimulation in the upper respiratory tract.

CONCLUSION

The results strongly indicate that S. equi strain TW 928 deletion mutant is safe in horses.

We claim:

1. Streptococcus equi strain TW 928, as deposited under number CBS 813.95 with the Centraalbureau voor Schimmelcultures at Baam, The Netherlands.

2. A microbiologically pure culture comprising the Streptococcus equi strain TW 928 according to claim 1.

3. A live vaccine for protection against Streptococcus equi infection, comprising the Streptococcus equi strain TW 928 according to claim 1, and a pharmaceutically acceptable carrier.

4. The vaccine according to claim 3, which is in a freeze-dried form.

5. The vaccine according to claim 3, further comprising another attenuated pathogen or antigenic material from another pathogen.

6. The vaccine according to claim 5, wherein said other pathogen is selected from the group consisting of Potomac fever agent, Rhodococcus equi, Clostridium tetanii, Mycobacterium pseudomallei, Vesicular Stomatitis Virus, Borna disease virus, Equine influenza virus, African horse sickness virus, Equine arteritis virus, Equine herpesvirus 1-4, Infectious anemia virus, Equine encephalomyelitis virus and Japanese B encephalomyelitis virus.

7. The vaccine according to claim 3, further comprising an adjuvant.

8. A method for the preparation of a vaccine according to claim 3, comprising admixing Streptococcus equi strain TW 928 with a pharmaceutically acceptable carrier, and recovering the mix of Streptococcus equi strain TW 928 and the pharmaceutically acceptable carrier.

9. The vaccine according to claim 7, wherein the adjuvant is selected from the group consisting of E. coli heat-labile toxin and Cholera toxin.

10. A method for immunizing against Streptococcus equi in horses, comprising administering to the horse the vaccine according to claim 3.

11. The method according to claim

UNITED STATES PATENT AND TRADEMARK OFFICE
CERTIFICATE OF CORRECTION

PATENT NO. : 5,895,654
DATED : APRIL 20, 1999
INVENTOR(S) : HARTFORD ET AL.

It is certified that error appears in the above-identified patent and that said Letters Patent is hereby corrected as shown below:

Line 11, column 10, delete Baam and insert -- Baarn --.

Signed and Sealed this

Third Day of August, 1999

Attest:

Q. TODD DICKINSON

*Attesting Officer*　　　*Acting Commissioner of Patents and Trademarks*